(12) United States Patent
Hsiao

(10) Patent No.: US 11,045,570 B2
(45) Date of Patent: Jun. 29, 2021

(54) SCENT DIFFUSER SYSTEM AND DEVICE ELECTRICALLY CHARGED IN WIRELESS MANNER

(71) Applicant: DONGGUAN YIH TEH ELECTRIC PRODUCTS CO., LTD., Dongguan (CN)

(72) Inventor: Ming Jen Hsiao, Miaoli County (TW)

(73) Assignee: DONGGUAN YIH TEH ELECTRIC PRODUCTS CO., LTD., Dongguan (CN)

( * ) Notice: Subject to any disclaimer, the term of this patent is extended or adjusted under 35 U.S.C. 154(b) by 316 days.

(21) Appl. No.: 16/157,994

(22) Filed: Oct. 11, 2018

(65) Prior Publication Data
US 2020/0114033 A1    Apr. 16, 2020

(51) Int. Cl.
*A61L 9/03* (2006.01)
*H02J 50/12* (2016.01)
*H02J 7/02* (2016.01)

(52) U.S. Cl.
CPC ............... *A61L 9/03* (2013.01); *H02J 7/025* (2013.01); *H02J 50/12* (2016.02)

(58) Field of Classification Search
CPC .............. A61L 9/03; H02J 50/13; H02J 7/025
USPC ................. 219/387, 628; 392/386, 390, 394
See application file for complete search history.

(56) References Cited

U.S. PATENT DOCUMENTS

| | | | |
|---|---|---|---|
| 8,983,277 B2 | 3/2015 | Hsiao | |
| 9,206,963 B2 | 12/2015 | Hsiao | |
| 9,410,695 B2 | 8/2016 | Hsiao | |
| 9,498,553 B2 | 11/2016 | Hsiao | |
| 9,500,358 B2 | 11/2016 | Hsiao | |
| 9,844,609 B2 | 12/2017 | Hsiao | |
| 10,064,969 B2 | 9/2018 | Hsiao | |
| 2015/0109823 A1* | 4/2015 | Hsiao | ........................ A61L 9/03 362/643 |
| 2015/0117056 A1 | 4/2015 | Hsiao | |
| 2016/0195257 A1 | 7/2016 | Hsiao | |
| 2017/0245679 A1* | 8/2017 | Watts | ................... H05B 6/1236 |

FOREIGN PATENT DOCUMENTS

CN        209137472       *   3/2018

\* cited by examiner

*Primary Examiner* — Thien S Tran
(74) *Attorney, Agent, or Firm* — Sinorica, LLC

(57) ABSTRACT

A scent diffuser device electrically charged in a wireless manner contains: an aromatic element, a wireless charger configured to convert first electric currents into electromagnetic signals, and a heater configured to receive and to convert the electromagnetic signals into second electric currents, by which the heater operates. The heater includes a case, a container, a heat insulator, a wireless charging receiver, and a heating unit. The case has an accommodation chamber, and the container has a holding space, a bottom fence, and a thermal conductor. The heat insulator includes two open segments so as to accommodate the container, the heating unit, and the thermal conductor. The holding space is configured to accommodate the aromatic element, and the wireless charger is electrically connected with a power supply so as to produce a magnetic field to send the electromagnetic signals and energy.

3 Claims, 7 Drawing Sheets

SCENT DIFFUSER SYSTEM AND DEVICE ELECTRICALLY CHARGED IN WIRELESS MANNER

FIELD OF THE INVENTION

The present invention relates to a scent diffuser system and device which are electrically charged in a wireless manner.

DESCRIPTION OF THE PRIOR ART

A conventional scent diffuser contains a heater configured to heat essential oil or scented wax in a wired manner, for example, the heater is electrically connected with a power port by using an electric wire, thus causing operational danger, such as electric shock. Furthermore, the heater is only applied to heat the essential oil or the scented wax.

A conventional scent diffuser system or device contains an electric wire connected with the heater, and the electric wire has to be removed as desiring to refill the essential oil/the scented wax or to clean the cent diffuser system or device.

In addition, the conventional scent diffuser system or device cannot electrically charge mobile device or other terminal devices.

The present invention has arisen to mitigate and/or obviate the afore-described disadvantages.

SUMMARY OF THE INVENTION

The primary aspect of the present invention is to provide a scent diffuser system and device which are electrically charged in a wireless manner and transmit energy by using a magnetic field so as to convert into electric energy to heat an aromatic element easily and safely.

Another aspect of the present invention is to provide a scent diffuser system and device which contains a wireless charger including multiple transmitting coil modules so as to heat the aromatic element or/and to electrically charge mobile devices or various terminal devices.

To obtain the above aspects, a scent diffuser system and device provided by the present invention contain: an aromatic element, a wireless charger, and a heater.

The aromatic element is selected from one of aromatic oil, essential oil, scented wax, essence, dry flower, and solid or fluid which is heated to scent.

The scent diffuser system includes the aromatic element, wireless charger, and the heater.

The wireless charger is configured to convert first electric currents into electromagnetic signals.

The heater is configured to receive the electromagnetic signals from the wireless charger and to convert the electromagnetic signals into second electric currents, by which the heater operates.

The heater includes a case, a container, a heat insulator, a wireless charging receiver, and a heating unit.

The case has an accommodation chamber defined inside an open end thereof, the container has a holding space defined therein, a bottom fence formed on a bottom of the container, and a thermal conductor, wherein the heat insulator includes two openings respectively formed on two sides thereof so as to accommodate the container, the heating unit, and the thermal conductor, wherein the heat insulator is connected inside the accommodation chamber, the container is located above the heat insulator, and the thermal conductor is fixed below the bottom fence, wherein the heating unit is mounted below the thermal conductor, and the wireless charging receiver is secured below the container and is electrically connected with the heating unit.

The holding space of the container of the heater is configured to accommodate the aromatic element, and the wireless charger is electrically connected with a power supply so as to produce a magnetic field to send the electromagnetic signals and energy, wherein the wireless charging receiver of the heater is close to the electromagnetic signals (i.e., the magnetic field) of the wireless charger so as to receive the electromagnetic signals and to transform the electromagnetic signals into the second electric currents, such that the heating unit heats the thermal conductor and the bottom fence of the container by using the second electric currents so that the holding space heats the aromatic element at a predetermined temperature, thus diffusing fragrance smell. After running out the aromatic element, it is easy to refill the aromatic element and to clean the container safely.

Preferably, the wireless charger includes multiple transmitting coil modules which are separately arranged in a charge board and are parallelly connected. When the heater is electrically charged, the multiple transmitting coil modules wirelessly charge mobile phones, wireless mice, or calculators.

A scent diffuser device is electrically charged in a wireless manner and contains: a heater including a case, a container, a heat insulator, a wireless charging receiver, and a heating unit.

The case has an accommodation chamber defined inside an open end thereof, the container has a holding space defined therein, a bottom fence formed on a bottom of the container, and a thermal conductor, wherein the heat insulator includes two openings respectively formed on two sides thereof so as to accommodate the container, the heating unit, and the thermal conductor, wherein the heat insulator is connected inside the accommodation chamber, the container is located above the heat insulator, and the thermal conductor is fixed below the bottom fence, wherein the heating unit is mounted below the thermal conductor, and the wireless charging receiver is secured below the container and is electrically connected with the heating unit.

Preferably, the scent diffuser device further contains: a wireless charger including at least one transmitting coil module which has a power circuit, a high-frequency oscillating circuit, and a high-frequency power amplifier circuit, wherein the power circuit is electrically connected with the high-frequency oscillating circuit and the high-frequency power amplifier circuit, and the wireless charging receiver of the heater includes a receiving coil module which has a high-frequency rectification filter circuit.

Preferably, the wireless charger further includes multiple transmitting coil modules which are separately arranged in a charge board and are parallelly connected. When the heater is electrically charged, the multiple transmitting coil modules wirelessly charge mobile phones, wireless mice, or calculators.

A scent diffuser device is electrically charged and receives in a wireless manner, and the scent diffuser device is an external wireless receiver and contains a heater including a built-in power interface electrically connected with the heating unit. The external wireless receiver is configured to electrically connect with the power interface by using various electric wires, thus obtaining using convenience.

DETAILED DESCRIPTION OF THE PREFERRED EMBODIMENTS

A scent diffuser system and device electrically charged in a wireless manner according to a preferred embodiment of the present invention comprise: an aromatic element 5, a wireless charger 1, and a heater 3.

The aromatic element 5 is selected from one of aromatic oil, essential oil, scented wax, essence, dry flower, and solid or fluid which is heated to scent.

Figure 1:
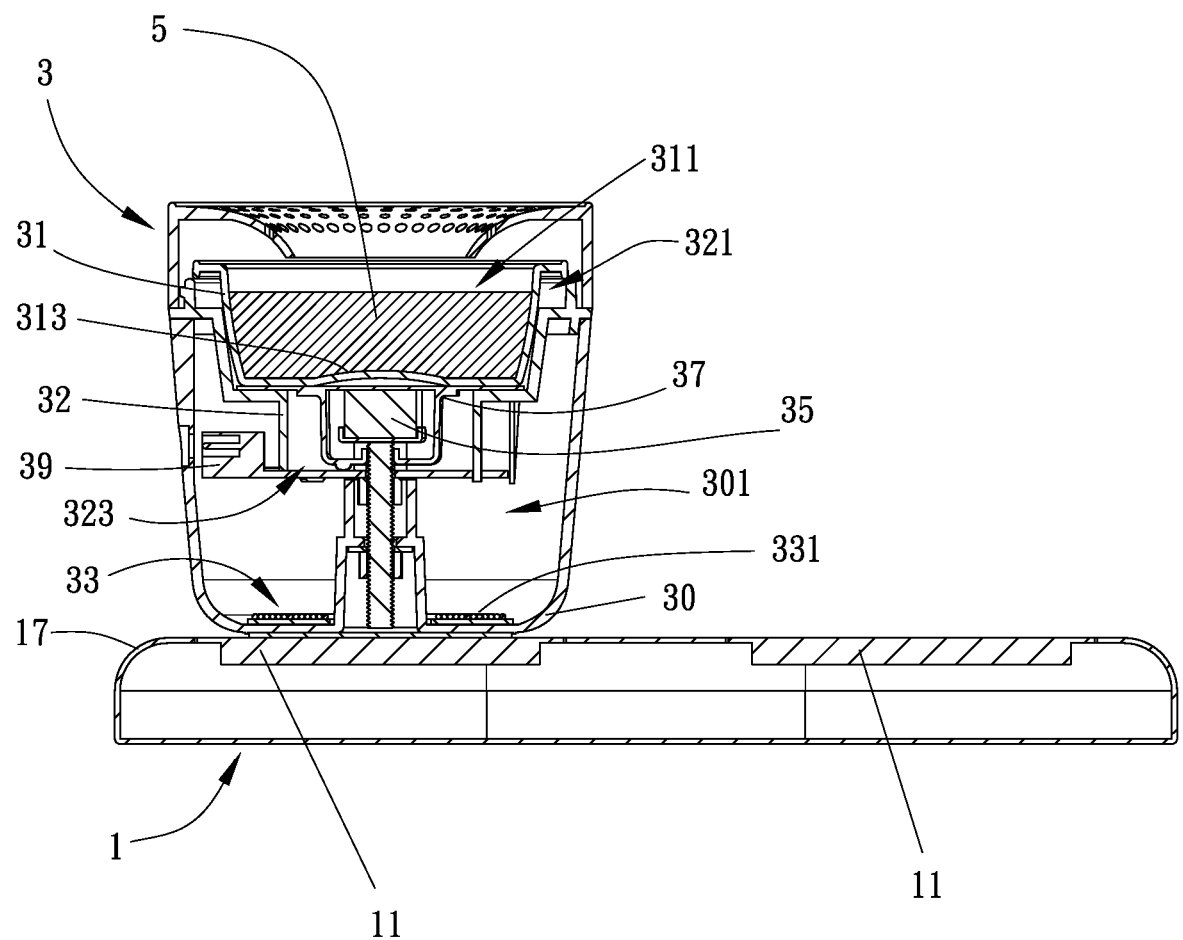
FIG. 1 is a cross sectional view showing the assembly of a scent diffuser system and device electrically charged in a wireless manner according to a preferred embodiment of the present invention.
Figure 2:
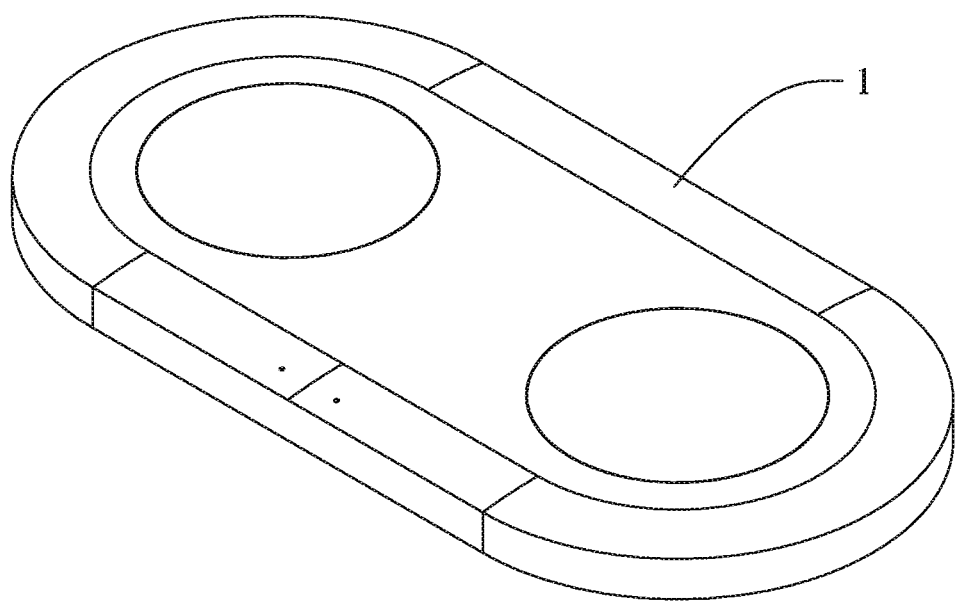
FIG. 2 is a perspective view showing the assembly of a wireless charger of the system and device according to the preferred embodiment of the present invention.
Figure 3:
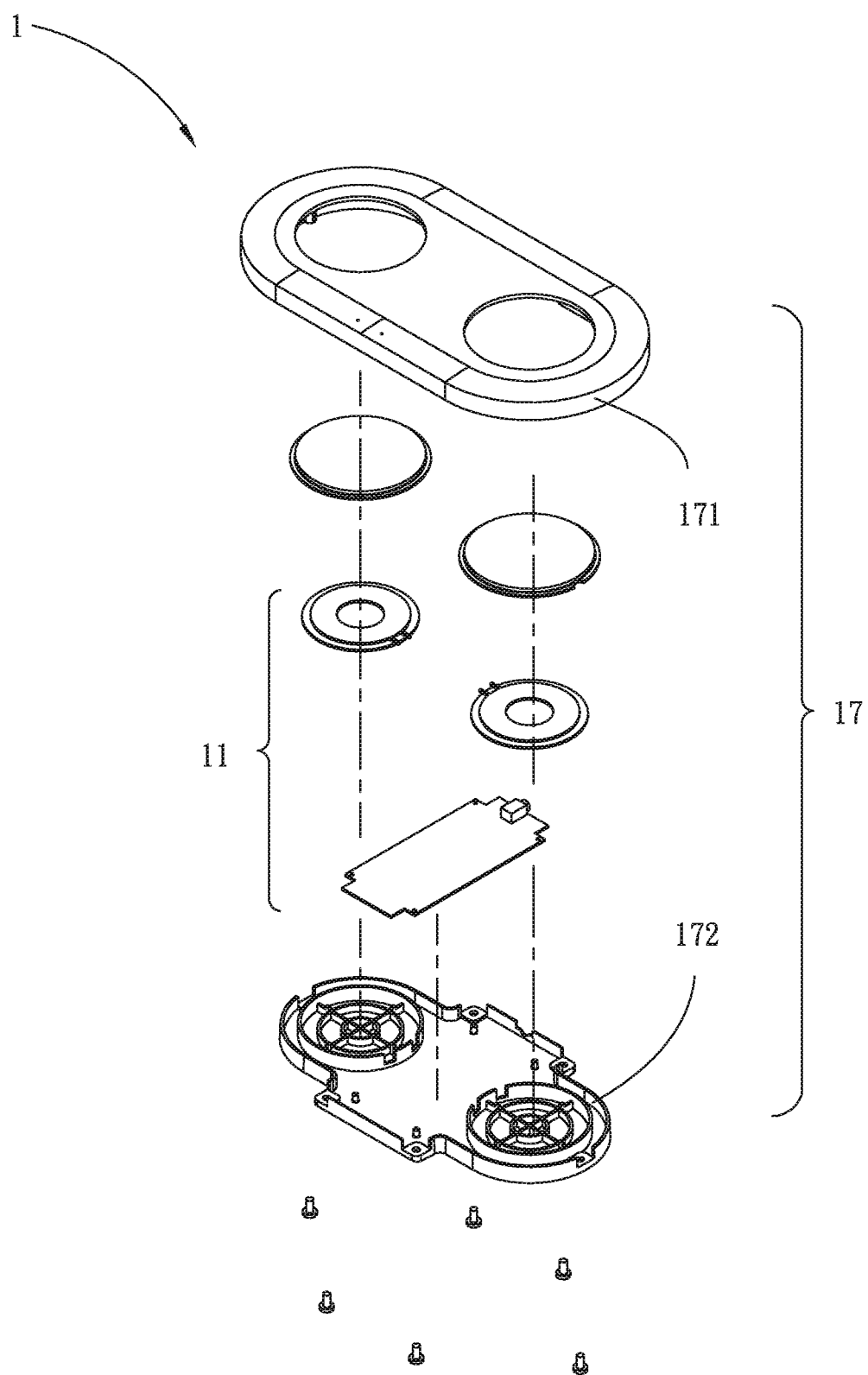
FIG. 3 is a perspective view showing the exploded components of the wireless charger of the system and device according to the preferred embodiment of the present invention.

With reference to FIGS. 1-3, the scent diffuser system electrically charged in the wireless manner according to the preferred embodiment of the present invention comprise: the aromatic element 5, the wireless charger 1, and the heater 3.

The wireless charger 1 is configured to convert first electric currents into electromagnetic signals.

The heater 3 is configured to receive the electromagnetic signals from the wireless charger 1 and to convert the electromagnetic signals into second electric currents, by which the heater 3 operates.

The heater 3 includes a case 30, a container 31, a heat insulator 32, a wireless charging receiver 33, and a heating unit 35. The case 30 has an accommodation chamber 301 defined inside an open end thereof. The container 31 has a holding space 311 defined therein, a bottom fence 313 formed on a bottom of the container 31, and a thermal conductor 37. The heat insulator 32 includes two openings 321 and 323 respectively formed on two sides thereof so as to accommodate the container 31, the heating unit 35, and the thermal conductor 37, wherein the heat insulator 32 is connected inside the accommodation chamber 301, the container 31 is located above the heat insulator 32, and the thermal conductor 37 is fixed below the bottom fence 313. The heating unit 35 is mounted below the thermal conductor 37, and the wireless charging receiver 33 is secured below the container 301 and is electrically connected with the heating unit 35.

The holding space 311 of the container 31 of the heater 3 is configured to accommodate the aromatic element 5, and the wireless charger 1 is electrically connected with a power supply so as to produce a magnetic field to send the electromagnetic signals and energy. The wireless charging receiver 33 of the heater 3 is close to the electromagnetic signals (i.e., the magmatic field) of the wireless charger 1 so as to receive the electromagnetic signals and to transform the electromagnetic signals into the second electric currents, such that the heating unit 35 heats the thermal conductor 37 and the bottom fence 313 of the container 31 by using the second electric currents so that the holding space 311 heats the aromatic element 5 at a predetermined temperature, thus diffusing fragrance smell.

The heat insulator 32 stops a heat source of the heating unit 35 being conducted to the wireless charging receiver 33, thus protecting the wireless charging receiver 33.

Thereby, the wireless charger 1 produces the magnetic field to send the energy, and the wireless charging receiver 33 of the heater 3 is close to the electromagnetic signals (i.e., the magmatic field) of the wireless charger 1 so as to receive (i.e., induce) the electromagnetic signals and to transform the electromagnetic signals into the second electric currents, such that the heating unit 35 heats the aromatic element 5 in the container 31 to scent the fragrant smell. After running out the aromatic element 5, it is easy to refill the aromatic element 5 and to clean the container 31 safely.

The wireless charger 1 is selected based on a variety of wireless charging standards, such as Wireless Power Consortium (i.e., Qi standard), Power Matters Alliance (PMA), and Alliance for Wireless Power (A4WP).

The heating unit 35 has various resistances, such as cement resistance or thermistor.

The thermal conductor 37 or the container 31 is selected from one of iron, copper, aluminum, ceramic, glass, and heat-resistant plastic.

Figure 4:
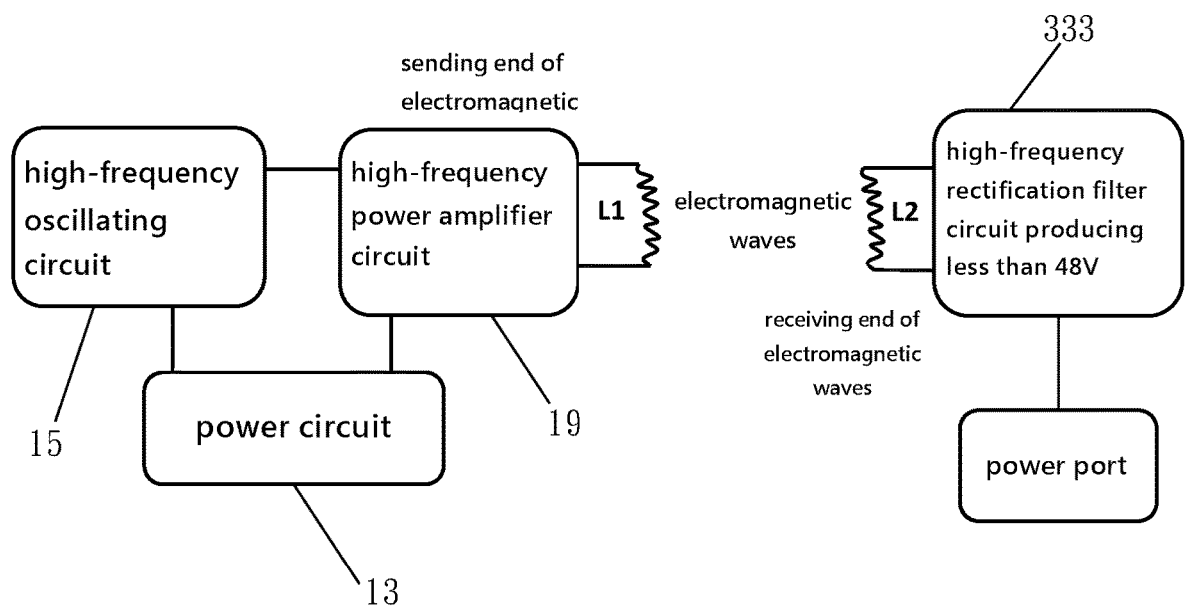
FIG. 4 is a block diagram showing the assembly of the wireless charger and the heater of the system and device according to the preferred embodiment of the present invention.

Referring to FIGS. 1, 3, and 4, the wireless charger 1 of the scent diffuser system and device includes at least one transmitting coil module 11 which has a power circuit 13, a high-frequency oscillating circuit 15, and a high-frequency power amplifier circuit 19, wherein the power circuit 13 is electrically connected with the high-frequency oscillating circuit 15 and the high-frequency power amplifier circuit 19 so as to excite and transmit electromagnetic waves.

The wireless charging receiver 33 of the heater 3 includes a receiving coil module 331 which has a high-frequency rectification filter circuit 333 configured to auxiliarily receive rectification voltage of the second electric currents.

Each of the at least one transmitting coil module 11 has a magnetic conductor and is configured to transmit a control circuit. The receiving coil module 331 has a receiving control circuit or a rectification regulator circuit so as to produce the magnetic field which couples with the receiving coil module, such that the receiving coil module 331 is connected with magnetic field signals, and the receiving control circuit of the receiving coil module 331 converts the magnetic field signals into power applicable for the heating unit 35.

As shown in FIGS. 1-3, the bottom fence 313 of the container 31 of the scent diffuser system and device is raised so as to avoid a heat source gathering on a central position of the bottom fence 313, such that the aromatic element 5 is not run out quickly. The container 31 is made of thermal conductive material, such as the heat-resistant plastic, the metal, the glass, and the ceramic.

Figure 5:
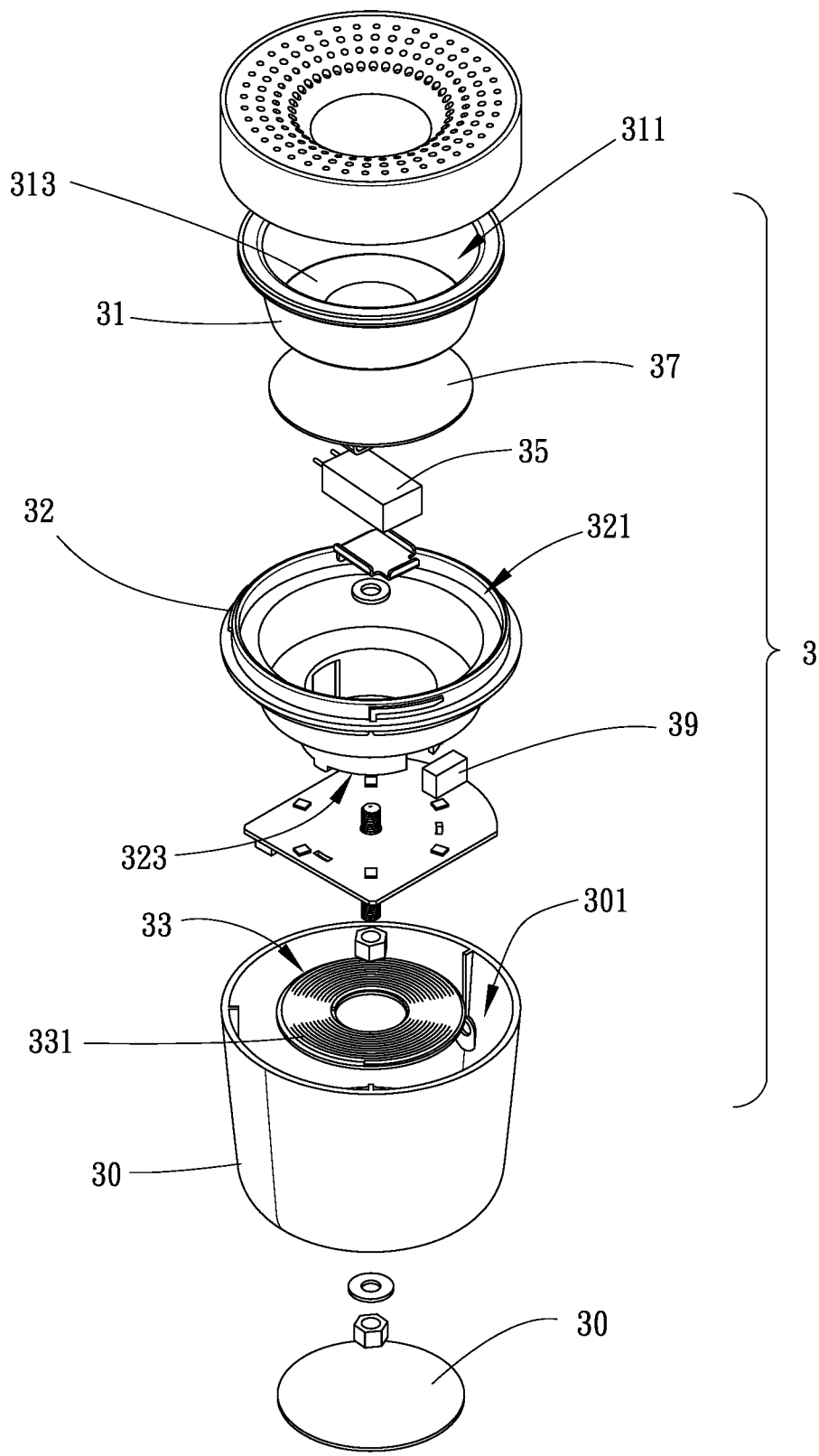
FIG. 5 is a perspective view showing the exploded components of a heater of the system and device according to the preferred embodiment of the present invention.

With reference to FIGS. 1, 3, and 5, the heater 3 of the scent diffuser system and device further includes a built-in power interface 39 formed on a side of the case 30 and electrically connected with the heating unit 35.

Referring to FIGS. 1-3, the wireless charger 1 of the scent diffuser system and device includes a charge board 17 which has a first lid 171 and a second lid 172 connected with the first lid 172, wherein the at least one transmitting coil module 11 of the wireless charger 1 is fixed in the charge board 17.

As illustrated in FIGS. 1-3, the wireless charger 1 of the scent diffuser system and device includes multiple transmitting coil modules 11 which are separately arranged in the charge board 17 and are parallelly connected so as to be charged wirelessly by mobile devices or terminal devices and to heat the aromatic element 5. When the heater 3 is electrically charged, the multiple transmitting coil modules 11 wirelessly charge mobile phones, wireless mice, or calculators.

As shown in FIGS. 1-3 and 5, the heater 3 of the scent diffuser system and device further includes a built-in power interface 39 formed on the side of the case 30 and includes a connection interface 335 electrically connected with the heating unit 35, wherein when the heater 3 is not electrically charged by the wireless charger 1, the connection interface 335 is electrically connected with the heater 3 via a power cable so as to supply the power to the heater 3 by ways of the connection interface 335.

As illustrated in FIGS. 1-3 and 5, the heater 3 of the scent diffuser device includes a case 30, a container 31, a heat insulator 32, a wireless charging receiver 33, and a heating unit 35. The case 30 has an accommodation chamber 301 defined inside an open end thereof. The container 31 has a holding space 311 defined therein and has a bottom fence 313 formed on a bottom of the container 31. The heat insulator 32 includes two openings 321 and 323 respectively formed on two sides thereof so as to accommodate the container 31 and the heating unit 35, wherein the container 31 is located above the heat insulator 32, the heating unit 35 is mounted below the bottom fence 313, and the wireless charging receiver 33 is secured below the container 301 and is electrically connected with the heating unit 35. The wireless charging receiver 33 of the heater 3 is close to the electromagnetic signals (i.e., the magmatic field) of the wireless charger 1 so as to couple with the electromagnetic signals and to transform the electromagnetic signals into the second electric currents, such that the heating unit 35 produces a heat source by using the second electric currents to heat the bottom fence 313 of the container 31 and to conduct a predetermined heat to the holding space 311.

With reference to FIGS. 1-7, the wireless charger 1 of the scent diffuser device further includes at least one transmitting coil module 11 which has a power circuit 13, a high-frequency oscillating circuit 15, and a high-frequency power amplifier circuit 19, wherein the power circuit 13 is electrically connected with the high-frequency oscillating circuit 15 and the high-frequency power amplifier circuit 19 so as to excite and transmit electromagnetic waves.

The wireless charging receiver 33 of the heater 3 further includes a receiving coil module 331 which has a high-frequency rectification filter circuit 333 configured to auxiliarily receive rectification voltage of the second electric currents. The receiving coil module 331 receives the electromagnetic signals (i.e., the magmatic field) of the at least one transmitting coil module 11 so as to couple with the electromagnetic signals and to transform the electromagnetic signals into the second electric currents, such that the heating unit 35 produces a heat source by using the second electric currents to heat the bottom fence 313 of the container 31 and to conduct a predetermined heat to the holding space 311.

Referring to FIGS. 1-5, the wireless charger 1 of the scent diffuser device includes multiple transmitting coil modules 11 which are separately arranged in the charge board 17 and are parallelly connected so as to be charged wirelessly by mobile devices or terminal devices and to heat the aromatic element 5. When the heater 3 is electrically charged, the multiple transmitting coil modules 11 wirelessly charge the mobile phones, wireless mice, or calculators.

As shown in FIGS. 1 and 5, the heater 3 of the scent diffuser device further includes a built-in power interface 39 formed on the side of the case 30 and electrically connected with the heating unit 35.

As shown in FIGS. 1 and 5, the heater 3 of the scent diffuser device further includes the thermal conductor 37 fixed below the bottom fence 313. The heating unit 35 is mounted below the thermal conductor 37, and the wireless charging receiver 33 is connected below the thermal conductor 37 which is configured to conduct the heat source of the heating unit 35 to the bottom fence 313 evenly so that the holding space 311 heats the aromatic element 5 equally.

As shown in FIGS. 1-5, the scent diffuser device is electrically charged and receives in the wireless manner, and the scent diffuser device further comprises a wireless charging receiver 33 configured to convert the second electric currents into the electromagnetic signals; and a heater 3 including a wireless receiver 330 configured to receive electromagnetic signals of the wireless charging receiver 33 and to covert the electromagnetic signals into the second electric currents.

As illustrated in FIGS. 2, 3, 5 and 6, the wireless charging receiver 33 of the scent diffuser system and device is an external wireless receiver 330, and the heater 3 includes a built-in power interface 39, a first side of which is electrically connected with the heating unit 35, and the wireless receiver 330 is in connection with a second side of the built-in power interface 39 by using an electrical cable. The wireless charger 1 is selected based on a variety of wireless charging standards, such as Wireless Power Consortium (i.e., Qi standard), Power Matters Alliance (PMA), and Alliance for Wireless Power (A4WP). Preferably, the external wireless receiver 330 is selected based on any one of Qi, PMA, and A4WP.

Thereby, the scent diffuser device is electrically charged and receives in the wireless manner, and the scent diffuser device comprises the heater 3 including a case 30, a container 31, a heat insulator 32, a heating unit 35, and a power interface 39. The case 30 has an accommodation chamber 301 defined inside an open end thereof. The container 31 has a holding space 311 defined therein and has a bottom fence 313 formed on a bottom of the container 31. The heat insulator 32 includes two openings 321 and 323 respectively formed on two sides thereof so as to accommodate the container 31 and the heating unit 35, wherein the container 31 is located above the heat insulator 32, the heating unit 35 is mounted below the bottom fence 313, and the power interface 39 is formed on a side of the case 30, and a side of the connection interface 335 is electrically connected with the heating unit 35.

Figure 6:
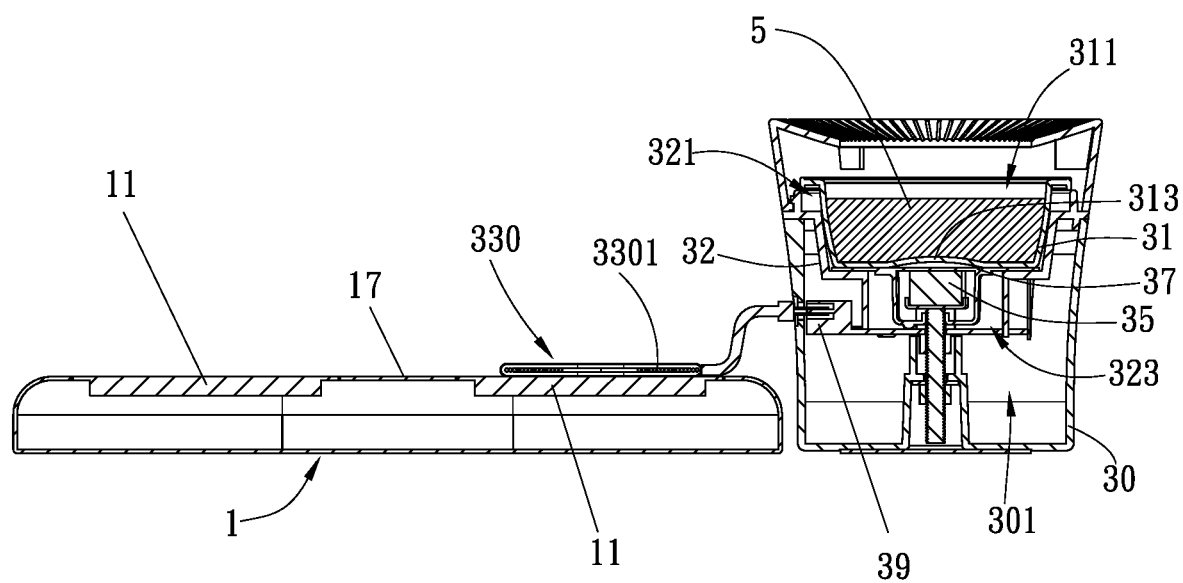
FIG. 6 is a cross sectional view showing the assembly of a scent diffuser system and device electrically charged in a wireless manner according to another preferred embodiment of the present invention.
Figure 7:
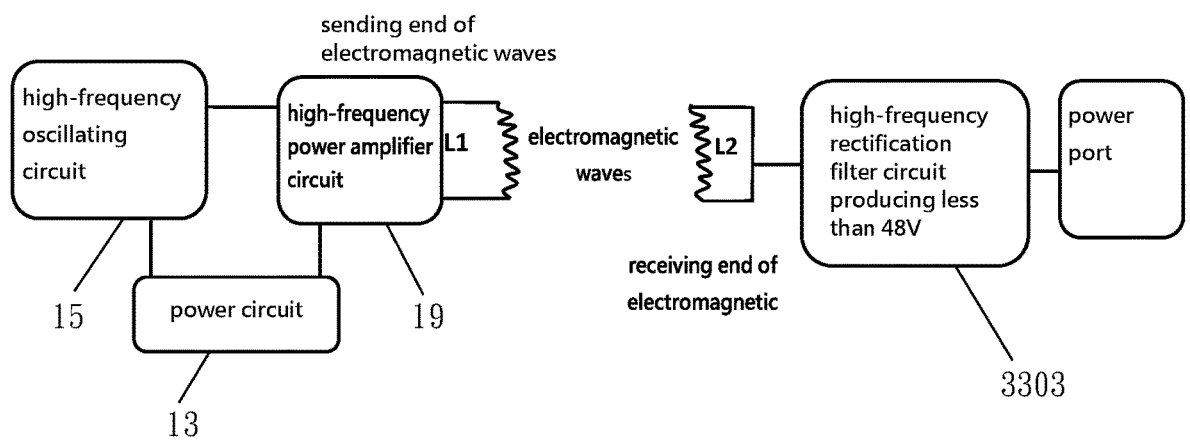
FIG. 7 is a block diagram showing the assembly of the wireless charger and the heater of the system and device according to another preferred embodiment of the present invention.

With reference to FIGS. 5 and 6, the scent diffuser device is electrically charged and receives in the wireless manner, and the scent diffuser device further comprises an external wireless receiver 330 configured to electrically connect with the power interface 39 by using various electric wires, such that the external wireless receiver 330 is closed to the electromagnetic signals (i.e., the magmatic field) of the wireless charger 1 so as to couple with, to receive (such as to induce or to resonantly receive) the electromagnetic signals, and to transform the electromagnetic signals into the second electric currents, such that the heating unit 35 heats the bottom fence 313 of the container 31 by using the second electric currents so that the bottom fence 313 conducts a predetermined heat to the holding space 311.

As illustrated in FIGS. 2-7, the scent diffuser device is electrically charged and receives in the wireless manner, and the scent diffuser device further comprises a wireless charger 1 including a transmitting coil module 11 which has a power circuit 13, a high-frequency oscillating circuit 15, and a high-frequency power amplifier circuit 19, wherein the power circuit 13 is electrically connected with the high-frequency oscillating circuit 15 and the high-frequency power amplifier circuit 19 so as to excite and transmit electromagnetic waves. The external wireless receiver 330 of the heater 3 includes a receiving coil module 3301 which has a high-frequency rectification filter circuit 3303 configured to auxiliarily receive rectification voltage of the second electric currents.

With reference to FIGS. 5 and 6, the scent diffuser device is electrically charged and receives in the wireless manner, and the heater 3 of the scent diffuser device further includes a thermal conductor 37 fixed below the bottom fence 313. The heating unit 35 is mounted below the thermal conductor 37, and the thermal conductor 37 is configured to conduct the heat source of the heating unit 35 to the container 31 and the holding space 311 evenly.

While the preferred embodiments of the invention have been set forth for the purpose of disclosure, modifications of the disclosed embodiments of the invention as well as other embodiments thereof may occur to those skilled in the art. The scope of the claims should not be limited by the preferred embodiments set forth in the examples, but should be given the broadest interpretation consistent with the description as a whole.

What is claimed is:

1. A scent diffuser system being electrically charged in a wireless manner and comprising:
   an aromatic element;
   a wireless charger configured to convert first electric currents into electromagnetic signals; and
   a heater configured to receive the electromagnetic signals from the wireless charger and to convert the electromagnetic signals into second electric currents, by which the heater operates;
   wherein the heater includes a case, a container, a heat insulator, a wireless charging receiver, and a heating unit;
   wherein the case has an accommodation chamber defined inside an open end thereof, the container has a holding space defined therein, a bottom fence formed on a bottom of the container, and a thermal conductor, wherein the heat insulator includes two openings respectively formed on two sides thereof so as to accommodate the container, the heating unit, and the thermal conductor, wherein the heat insulator is connected inside the accommodation chamber, the container is located above the heat insulator, and the thermal conductor is fixed below the bottom fence, wherein the heating unit is mounted below the thermal conductor, and the wireless charging receiver is secured below the container and is electrically connected with the heating unit;
   wherein the holding space of the container of the heater is configured to accommodate the aromatic element, and the wireless charger is electrically connected with a power supply so as to produce a magnetic field to send the electromagnetic signals and energy, wherein the wireless charging receiver of the heater is close to the electromagnetic signals of the wireless charger so as to receive the electromagnetic signals and to transform the electromagnetic signals into the second electric currents, such that the heating unit heats the thermal conductor and the bottom fence of the container by using the second electric currents so that the holding space heats the aromatic element at a predetermined temperature, thus diffusing fragrance smell.

2. The scent diffuser system as claimed in claim 1, wherein the wireless charger includes a transmitting coil module which has a power circuit, a high-frequency oscillating circuit, and a high-frequency power amplifier circuit, wherein the power circuit is electrically connected with the high-frequency oscillating circuit and the high-frequency power amplifier circuit, and the wireless charging receiver of the heater includes a receiving coil module which has a high-frequency rectification filter circuit.

3. The scent diffuser system as claimed in claim 2, wherein the wireless charger further includes multiple transmitting coil modules which are separately arranged in a charge board and are parallelly connected.

* * * * *